(12) United States Patent
Kuraguntla et al.

(10) Patent No.: US 11,006,845 B2
(45) Date of Patent: May 18, 2021

(54) SYSTEM AND METHOD FOR MEASURING BLOOD FLOW PARAMETERS IN A BLOOD VESSEL HAVING AN ENDOVASCULAR PROSTHESIS

(71) Applicant: GRAFTWORX, INC., South San Francisco, CA (US)

(72) Inventors: David Kuraguntla, Bel Air, MD (US); Samit Kumar Gupta, Menlo Park, CA (US); Lilip Lau, Los Altos, CA (US); Anthony F. Flannery, Bainbridge Island, WA (US)

(73) Assignee: Graftworx, Inc., San Francisco, CA (US)

( * ) Notice: Subject to any disclaimer, the term of this patent is extended or adjusted under 35 U.S.C. 154(b) by 169 days.

(21) Appl. No.: 16/316,403

(22) PCT Filed: Jul. 12, 2017

(86) PCT No.: PCT/US2017/041773
§ 371 (c)(1),
(2) Date: Jan. 9, 2019

(87) PCT Pub. No.: WO2018/013725
PCT Pub. Date: Jan. 18, 2018

(65) Prior Publication Data
US 2019/0246916 A1 Aug. 15, 2019

Related U.S. Application Data

(60) Provisional application No. 62/361,384, filed on Jul. 12, 2016.

(51) Int. Cl.
*A61F 2/82* (2013.01)
*A61B 5/0265* (2006.01)
(Continued)

(52) U.S. Cl.
CPC .......... *A61B 5/0265* (2013.01); *A61B 5/0031* (2013.01); *A61B 5/026* (2013.01);
(Continued)

(58) Field of Classification Search
CPC ................ A61F 2/82; A61F 2250/0002; A61F 2250/0001; A61F 2/88; A61F 2250/0045;
(Continued)

(56) References Cited

U.S. PATENT DOCUMENTS 6,206,835 B1   3/2001   Spillman, Jr. et al.
7,307,530 B2   12/2007  Fabian et al.
(Continued)

FOREIGN PATENT DOCUMENTS

WO   WO-2018013725 A1   1/2018

OTHER PUBLICATIONS

"International Application Serial No. PCT/US2017/041773, International Search Report dated Sep. 26, 2017", 2 pgs.
(Continued)

*Primary Examiner* — Brian E Pellegrino
(74) *Attorney, Agent, or Firm* — Jonathan D. Feuchtwang

(57) ABSTRACT

Systems and methods for remotely monitoring blood flow that include an endovascular prosthesis. The endovascular prosthesis includes a conduit forming a lumen within a surrounding wall having an inner surface and an outer surface. A monitoring device is disposed on the wall forming the lumen. The monitoring device comprises a sensor element configured to detect a physical event and to generate an electrical parameter shift in response to the physical event. An antenna portion is configured to receive a first oscillating electrical signal from an interrogator device and to transmit a second oscillating electrical signal to the interrogator device. The second oscillating electrical signal is modulated by the electrical parameter shift.

12 Claims, 10 Drawing Sheets

(51) Int. Cl.
  *A61B 5/00* (2006.01)
  *A61F 2/06* (2013.01)
  *A61F 2/88* (2006.01)
  *A61B 5/026* (2006.01)

(52) U.S. Cl.
  CPC .............. *A61B 5/6862* (2013.01); *A61F 2/06* (2013.01); *A61F 2/82* (2013.01); *A61F 2/88* (2013.01); *A61F 2250/0002* (2013.01)

(58) Field of Classification Search
  CPC ........... A61F 2/915; A61F 2310/00395; A61B 5/0265; A61B 5/6862
  See application file for complete search history.

(56) References Cited

U.S. PATENT DOCUMENTS

| | | | |
|---|---|---|---|
| 7,452,334 | B2 | 11/2008 | Gianchandani et al. |
| 8,054,140 | B2 | 11/2011 | Fleming et al. |
| 2003/0053284 | A1 | 3/2003 | Stevenson et al. |
| 2005/0273014 | A1* | 12/2005 | Gianchandani ........... G01F 1/56 600/505 |
| 2009/0264762 | A1* | 10/2009 | Keilman ................. A61B 5/026 600/455 |
| 2010/0179449 | A1 | 7/2010 | Chow et al. |
| 2014/0214149 | A1* | 7/2014 | Kuraguntla .......... A61B 5/6862 623/1.15 |
| 2016/0022447 | A1* | 1/2016 | Kim ......................... A61F 2/88 623/1.15 |

OTHER PUBLICATIONS

"International Application Serial No. PCT/US2017/041773, Written Opinion dated Sep. 26, 2017", 6 pgs.

Park, J, et al., "A Wireless Pressure Sensor Integrated with a Biodegradable Polymer Stent for Biomedical Applications", Sensors 2016, 16, 809-818, Figures 1 a, 2b, 5a, 6a, 6c, 7a, (Jun. 2, 2016), 2-10.

* cited by examiner

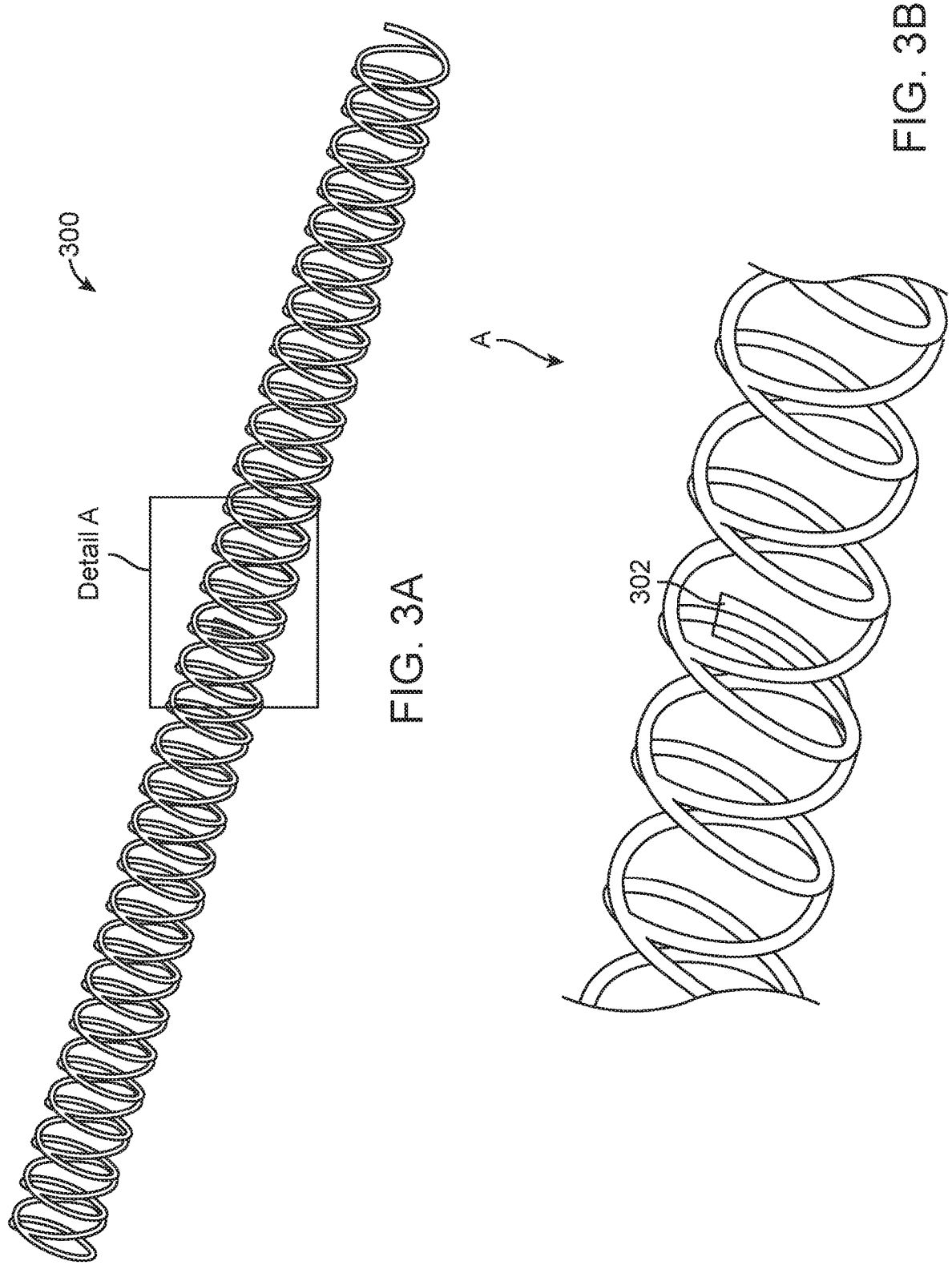

SYSTEM AND METHOD FOR MEASURING BLOOD FLOW PARAMETERS IN A BLOOD VESSEL HAVING AN ENDOVASCULAR PROSTHESIS

PRIORITY CLAIM AND INCORPORATION BY REFERENCE

This application is a U.S. National Stage Filing under 35 U.S.C. 371 from International Application No. PCT/US2017/041773, filed on Jul. 12, 2016, and published as WO 2018/013725 A1 on Jan. 18, 2018, which claims the priority of provisional application 62/361,384, titled "System and Method for Measuring Blood Flow Parameters in a Blood Vessel having an Endovascular Prosthesis," filed on Jul. 12, 2016, the contents of which are incorporated by reference herein.

The following patent applications are incorporated herein by reference: U.S. Provisional Patent Application Ser. No. 62/130,465, titled "Sensor Position on a Prosthesis for Detection of a Stenosis," filed on Mar. 9, 2015; U.S. Provisional Patent Application Ser. No. 62/129,666, titled "Detection of Stenosis in a Prosthesis using Break Frequency," filed on Mar. 6, 2015; and U.S. Non-Provisional patent application Ser. No. 15/208,225, titled "PASSIVE SENSOR TAG SYSTEM" filed on Jul. 12, 2016.

BACKGROUND

1. Field of the Invention

The disclosed systems and methods relate to the use of endovascular prosthetics to treat stenosis in blood vessels, and more particularly, to systems and methods for monitoring blood flow through the endovascular prosthetics.

2. Background

A stent is a tubular prosthesis often used for treating arterial stenosis by inserting a mechanical device (stent) into the artery to re-establish an acceptable open diameter to support adequate blood flow. One challenge associated with the use of stents is that restenosis often occurs at the location of the stent. It is desirable to monitor the level of occlusion and intervene with a less invasive procedure such as angioplasty or re-stenting before the occlusion reaches a more critical level that requires more catastrophic intervention such as amputation or a bypass.

Current methods of monitoring the level of occlusion require an office visit and diagnostic procedure such as Doppler ultrasound or CT angiogram. Consequently the interval of monitoring is practically limited. The cost of these tests is also a factor. Skilled personnel must perform the tests and interpret the results. Devices that may be implanted have been considered for constant monitoring of blood flow in situ. The main drawback of such devices lies in their need for a power source. Two main factors make the incorporation of a power source within the device impractical: geometry and safety. The size of intraluminal arterial stents is small enough that batteries with adequate capacity are not possible. In addition, the possibility of a battery rupture and leaking potentially toxic components into the bloodstream is also a concern.

There is a need in the art for a method of monitoring the level of occlusion on a regular basis without the need for an office visit or intervention by skilled personnel.

SUMMARY

In view of the above, examples of methods and systems are described below for remotely monitoring blood flow in an endovascular prosthesis.

In one aspect, an endovascular prosthesis comprises a conduit forming a lumen within a surrounding wall having an inner surface and an outer surface; and a monitoring device disposed on the wall forming the lumen. The monitoring device comprises a sensor element configured to detect a physical event and to generate an electrical parameter shift in response to the physical event, and an antenna portion configured to receive a first oscillating electrical signal from an interrogator device and to transmit a second oscillating electrical signal to the interrogator device where the second oscillating electrical signal can be modulated by the electrical parameter shift.

The endovascular prosthesis may further comprise a sensor controlled oscillator configured to generate the second oscillating electrical signal where the electrical parameter shift of the sensor element determines a modulated frequency of the second electrical signal.

The sensor controlled oscillator may be a passive resonant circuit, where the electrical parameter shift by the sensor element in response to the physical event is a change in capacitance that varies the modulated frequency of the second oscillating electrical signal. The passive resonant circuit may be a ring oscillator.

The sensor controlled oscillator may be a resistor controlled oscillator, where the electrical parameter shift by the sensor element in response to the physical event is a change in resistance that varies the modulated frequency of the second oscillating electrical signal.

The sensor controlled oscillator may be a voltage controlled oscillator, where electrical parameter shift by the sensor element in response to the physical event is a change in resistance that varies the modulated frequency at the output of the voltage controlled oscillator.

The sensor element may be any one of either a piezoresistive sensor, a piezoelectric strain gauge, or a variable capacitive sensor.

The endovascular prosthesis may further comprise a passive power source configured to collect and store electrical energy from the first oscillating electrical signal.

The endovascular prosthesis may further comprise a radio frequency identification detection mechanism configured to transmit an identifier of the device when energized by the first electrical oscillating signal.

The wall of the endovascular prosthesis may be formed by at least one of the following: a plurality of coaxially disposed rings connected by at least one link; a helix structure; a braided structure; a coil structure; a structure of interconnected struts; and the monitoring device is disposed on the wall of the endovascular prosthesis.

The endovascular prosthesis may comprise at least one component of the monitoring device integrated within a structure of the endovascular prosthesis. The sensor element may be an integrated sensor element formed as a coaxial capacitor comprising a first metallic conduit, a second metallic conduit, and a sensor material that changes in capacitance when subject to pressure or stress, the coaxial capacitor forming at least a portion of a wire or strut element configured to form the wall structure of the endovascular prosthesis. In another embodiment, the sensor element may be an integrated sensor element formed as a variable resistor comprising a sensor material that varies in resistance when subject to pressure or stress disposed between a first metallic conduit and a second metallic conduit, the variable resistor forming at least a portion of a wire or strut element configured to form the wall structure of the endovascular prosthesis. At least a portion of the endovascular prosthesis may be made of a metal, and at least a portion of the endovascular prosthesis made of metal is configured to operate as the antenna portion of the monitoring device.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The novel features believed characteristic of the illustrative examples are set forth in the appended claims. The illustrative examples, however, will best be understood by reference to the following detailed description of an illustrative example of the present disclosure when read in conjunction with the accompanying drawings, wherein:

FIGS. 3A and 3B illustrate an example of an endovascular prosthesis with a monitoring device disposed on the wall of the endovascular prosthesis.

DETAILED DESCRIPTION

Figure 1A:
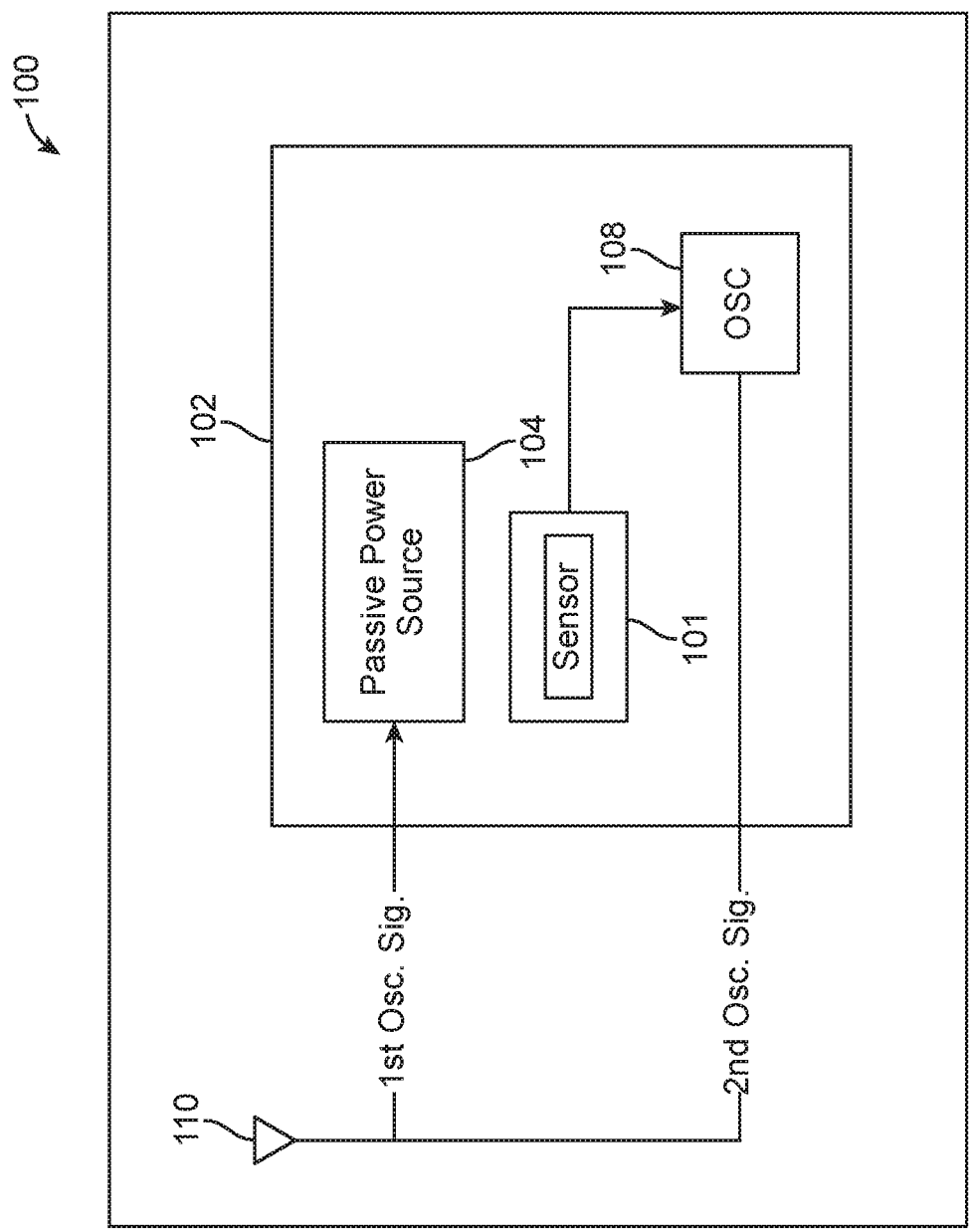
FIG. 1A is a schematic diagram of an example of a remote blood monitoring system.

FIG. 1A is a schematic diagram of an example of an endovascular prosthesis 100 having a remote blood-monitoring device 102. The endovascular prosthesis 100 comprises a conduit forming a lumen within a surrounding wall having an inner surface and an outer surface. The endovascular prosthesis 100 is illustrated schematically as a box in FIG. 1A; however, the structure of the endovascular prosthesis 100 is described below with reference to FIGS. 3A-10B. The remote blood-monitoring device 102 is disposed on the wall forming the lumen in a variety of ways as described below. The monitoring device 102 comprises a sensor element 101 configured to detect a physical event and to generate an electrical parameter shift in response to the physical event. An antenna portion 110 receives a first oscillating electrical signal from an interrogator device, described below with reference to FIG. 2. The antenna portion 110 may also be used to transmit a second oscillating electrical signal to the interrogator device where the second oscillating electrical signal is modulated by the electrical parameter shift.

The monitoring device 104 may include a passive power supply 104, which provides electrical power by storing energy from receiving the first oscillating electrical signal. The passive power supply 104 may comprise a resonator coupled to a rectifier. The first oscillating electrical signal may excite the resonator to generate a resonating electrical signal. The resonating electrical signal is received by the rectifier and converted to a charge stored until needed to provide a DC voltage.

The monitoring device 102 in FIG. 1A includes a sensor controlled oscillator 108 configured to generate the second oscillating electrical signal modulated by the sensor element 101. The modulated second oscillating signal is transmitted via the antenna portion 110 to the interrogator device.

The sensor element 101 may be any suitable sensor device that operates as a transducer of one form of energy to electrical energy. The sensor element 101 may be sensitive to any suitable physical event. In examples described herein, the monitoring device 102 monitors parameters which can be useful for indirectly determining blood flow and the sensor element 101 used would be sensitive to a physical event relevant to blood flow and generate an electrical parameter shift corresponding to the physical event. For example, the electrical parameter shift may be in response to pressure or strain on the sensor element 101 caused by the flow of blood contacting the sensor element 101. In another example, the sensor element 101 may be sensitive to heat and provide a thermal flow measurement. In one approach a sensor element is heated above the ambient. The amount of energy it takes to maintain that temperature is directly related to the rate of flow across that sensor element. In another approach, a sensor element element is heated above ambient. The amount of heat that is carried to an adjacent sensor element is detected by monitoring its temperature, and is directly related to flow.

It is noted that multiple sensor elements 101 may be used instead of a single sensor element. In an example implementation, differential measurements may be taken of two sensor elements 101 to predict flow.

The sensor element 101 in some example implementations include, without limitation, any one of either a piezoresistive sensor, a piezoelectric strain gauge, or a variable capacitive sensor. Examples of configurations of each of these types of sensor elements are described below.

The sensor-controlled oscillator 108 may be implemented using different types of circuits. In one example implementation, the sensor-controlled oscillator 108 is a passive resonant circuit, where the electrical parameter shift by the sensor element 101 in response to the physical event is a change in capacitance. The sensor element 101 may be a variable capacitor in which the capacitance varies in response to the pressure of the blood flow in contact with the sensor element 101. The sensor element 101 implemented as a variable capacitor may be connected in an oscillator circuit that generates the second oscillating electrical signal when energized, for example, by the passive power supply 104. As is well known in the art, the frequency of the second oscillating electrical signal depends on at least the capacitance of the oscillator circuit. As the capacitance varies, the generated frequency varies as well providing an indication of, for example, a pressure gradient in the endovascular prosthesis 100. As such, the varied frequency is essentially modulated in accordance with the physical event, such as, for example, the pressure. In an example implementation, the passive resonant circuit is a ring oscillator.

In another example implementation, the sensor controlled oscillator 108 is a resistor controlled oscillator, where the electrical parameter shift by the sensor element in response to the physical event is a change in resistance that varies the modulated frequency of the second oscillating electrical signal. The sensor element 101 may in this example be a piezoresistive element. The implementation of a resistor-controlled oscillator is similar to that of the passive resonant circuit described above in which the modulated frequency of the second oscillating electrical signal depends on capacitance. In either example, the passive resonant circuit may be a simple RLC circuit known to those of ordinary skill in the art. The inductor of the passive RLC circuit may be derived from the structure of the endovascular prosthesis 100 itself, taking advantage of the inherent inductance of the one or more conductive elements of the device. Alternatively, it may be co-fabricated with the other elements of the system using similar thin film techniques. For example, a ferromagnetic material such as permalloy may be deposited in a coil pattern to produce a structure of sufficient inductance to satisfy the requirements of the circuit. In an alternative implementation, the passive resonant circuit may employ a crystal, or employ a Micro-Electro-Mechanical structure (MEMS), or a mechanical resonator.

In examples described herein, the resistance, inductive, and capacitance elements may be parts of the structure of the endovascular prosthesis 100 that provides structural support for blood vessels suffering from stenosis. In one example implementation, the resistor-controlled oscillator 108 is a Wein Bridge Oscillator.

In another example implementation, the sensor controlled oscillator 108 is a voltage controlled oscillator, where electrical parameter shift by the sensor element in response to the physical event is a change in resistance that varies the modulated frequency at the output of the voltage controlled oscillator. The sensor element 101 implemented as a variable resistance element may be connected in a voltage divider, or similar passive circuit that provides a voltage to the voltage controlled oscillator. The voltage may be dependent initially on the voltage provided by the passive power supply 104 and as the blood flow contacting the sensor element 101 causes a change in the resistance of the sensor element 101 the change in the voltage input to the voltage controlled oscillator causes the frequency output of the voltage controlled oscillator. The voltage controlled oscillator implementation of the sensor controlled oscillator 108 may be implemented as an active circuit powered by the passive power supply 104. The circuit forming the remote blood-monitoring device 102 may be implemented as a semiconductor element having the circuit elements etched on a silicon or other suitable substrate. The circuit may also be printed on a thin-film substrate.

It is noted that the above-described examples of sensor-controlled oscillators 108 are provided as examples of the types of oscillators that may be used in example implementations. The examples are described without limiting implementations to any specific type.

Figure 1B:
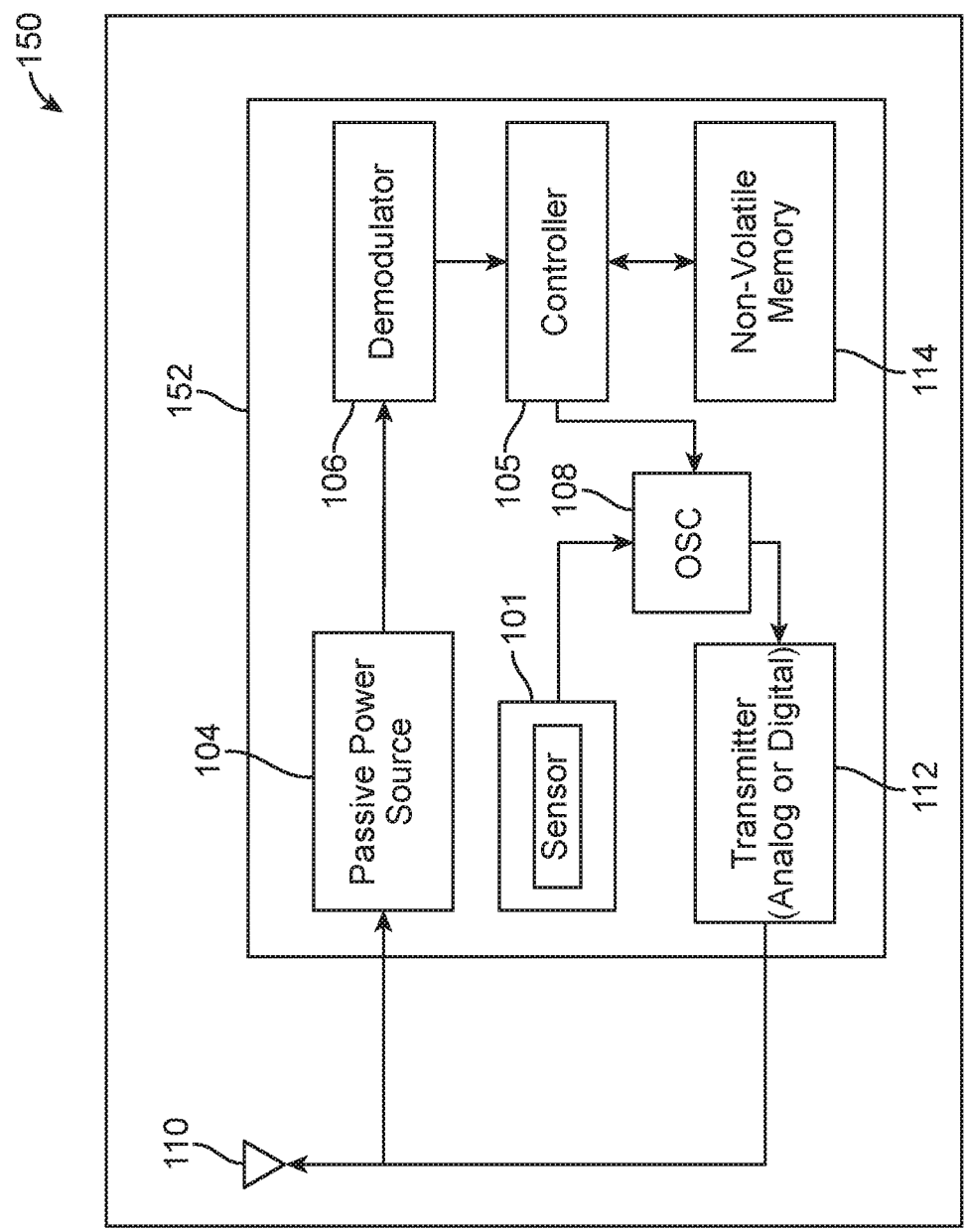
FIG. 1B is a schematic diagram of another example of a remote blood monitoring system.

FIG. 1B is a schematic diagram of another example of an endovascular prosthesis 150 incorporating a remote blood-monitoring device 152. The remote blood-monitoring device 152 in FIG. 1B includes the sensor element 101, the oscillator 108, and the passive power supply 104, which operates as described above with reference to FIG. 1A. The remote blood-monitoring device 152 in FIG. 1B also includes a controller 105, a demodulator 106, a transmitter element 112, and a non-volatile memory element 114.

In the remote blood-monitoring device 152 shown in FIG. 1B, the passive power source 104 receives the first oscillating electrical signal and uses it to generate power as described above with reference to FIG. 1A. The first oscillating electrical signal is also modulated with an identifier, or a command, such as a radio frequency identifier ("RFID"). The electrical signal may be modulated with a command and an identifier. The demodulator 106 receives the first oscillating signal and demodulates the signal to obtain the RFID and/or command, and communicates the RFID to the controller 105. The controller 105 executes the command, which may be instructions to program the non-volatile memory element 114 with the RFID. The controller 105 communicates the RFID to the non-volatile memory element 114 in the monitoring device 152, where the RFID is stored. The non-volatile memory 114 may be implemented as embedded non-volatile memory (eNVM) such as EEPROM, Flash, nano-fuse, or other suitable alternatives. The controller 105 may be implemented using any suitable processor executing a program with the necessary logic. A low-power processing implementation is preferred. A device having combinatorial logic may be sufficient. In another example, the non-volatile memory 114 may be pre-programmed with an identifier or code and the controller 105 may be instructed to simply read the identifier.

The controller 105 may also read the RFID or other identifier from the non-volatile memory 114. The controller 105 may modulate the second oscillating signal generated by the oscillator 108. The second oscillating signal is also modulated as described above with reference to FIG. 1A by the sensor 101. The modulation by the controller 105 to carry the RFID or the identifier may be phased in with the modulation of the second oscillating signal by the sensor 101. For example, the controller 105 may disable modulation by the sensor 101 while the identifier is communicated to the oscillator 108. The identifier may be encoded by controlling the oscillator 108 to send a '1' bit at one frequency and a '0' bit at another frequency. The different frequencies may be generated by switching in or out selected passive components that modify the frequency output of the oscillator 108.

In an example implementation, the identifier or code may be protected from being re-programmed by adding a security bit to the code.

The transmitter element 112 may be either an analog transmitting device, or a digital transmitting device. The analog transmitting device may include a simple output connection to the antenna 110, or a passive filter if desired, or an amplifying device if desired. In addition, while modulation of the second oscillating signal may involve varying the frequency of the second oscillating signal as described above with reference to FIG. 1A based on the sensor element 101, the second oscillating signal may also be modulated by varying the signal's amplitude. Amplitude modulation may be performed by adding a voltage divider having a piezoresistive element or another suitable resistive varying sensor element 101 at the output of the oscillator 108.

The transmitter element 112 may also be a digital transmitter that includes an analog to digital converter ("ADC"). The ADC samples and converts the second oscillating signal into a digital stream. The digital stream is encoded into a signal and transmitted out of the body.

Figure 2:
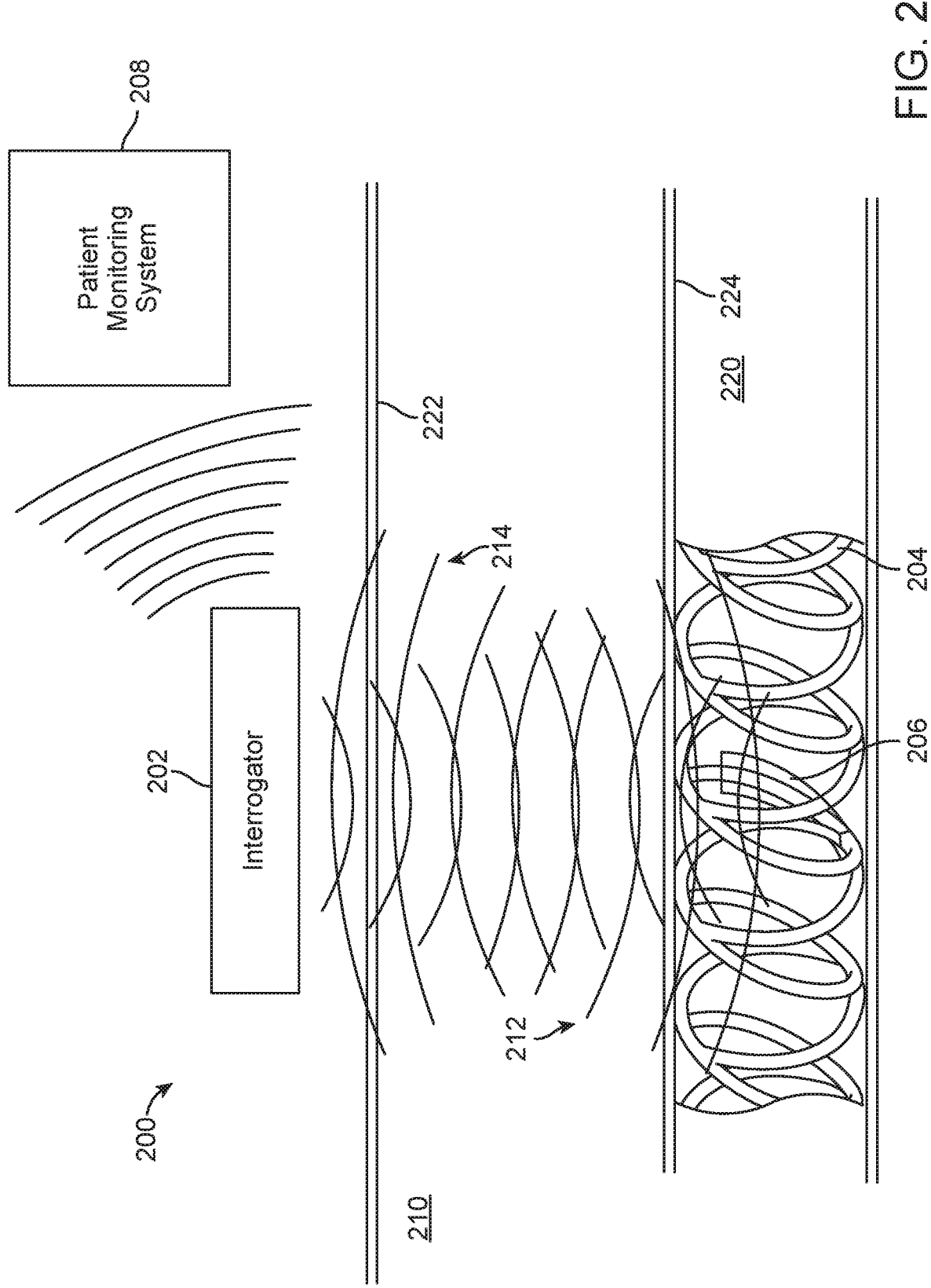
FIG. 2 is a schematic diagram illustrating operation of a blood flow monitoring system using an example of a remote blood-monitoring device.

As noted above, the monitoring device 102 in FIG. 1A is interrogated by an interrogator via reception of the first oscillating electrical signal. The interrogator then receives data relating to the blood flow through the endovascular prosthesis 100 in the second oscillating electrical signal. FIG. 2 is a schematic diagram illustrating operation of a blood flow monitoring system 200 using an example of the remote blood-monitoring device. The system 200 in FIG. 2 includes an interrogator 202, or reader device, an endovascular prosthesis 204 operably inserted into a blood vessel 220, and a monitoring device 206 disposed in a structure forming the wall of the endovascular prosthesis 204. The interrogator 202 is positioned near the patient's skin 222 during operation. The interrogator 202 emits the first oscillating electrical signal 212, which is transmitted through the patient's skin 222 and tissue 210 towards the blood vessel 220 in the area of the endovascular prosthesis 204. The monitoring device 206 is mounted, or formed on a wire, or strut structure forming the wall of the endovascular prosthesis 204. The monitoring device 206 receives the first oscillating electrical signal 212 as described above with reference to FIG. 1A. The monitoring device 206 generates the second oscillating electrical signal 214 as described above to be received by the interrogator 202. The interrogator 202 may simply relay the second oscillating electrical signal 214 using a higher power signal to a patient monitoring system 208. The patient monitoring system 208 may then analyze the second oscillating electrical signal 214 to determine changes in blood flow pressure. Further analysis of a history of readings may provide indications of a re-stenosis of the endovascular prosthesis 204. By sampling the pressure of flow with sufficiently high resolution, the signal (e.g. frequency/amplitude) can be analyzed to determine the level of occlusion of the blood vessel.

As shown in FIG. 2, the monitoring device 206 is disposed on the wall of the endovascular prosthesis 204. The monitoring device 206 may be formed on an integrated circuit and mounted on the structure of the wall, or in some implementations, integrated into the structure forming the endovascular prosthesis. The integrated circuit may be mounted on a flexible film of materials that form a variable capacitor or a variable resistor or have piezoelectric properties. The flexible film may then be mounted or attached to a structure forming the wall of the endovascular prosthesis. The integrated circuit may include electronic components necessary for the function of the circuitry comprising the monitoring device 206 except for components formed as part of the endovascular prosthesis 204. In one example, the endovascular prosthesis 204 structure is used as an antenna portion for receiving and transmitting RF signals as described above. This example may entail modifying the stent to enhance the performance of the stent as an antenna. The antenna portion may also be fabricated separately and integrated onto the stent in assembly of the device. In another example, the sensor element 206 may be integrated into the structure of the endovascular prosthesis 204. In one example of the sensor element 206 integrated into the endovascular prosthesis 204, the sensor element 206 may be a coaxial capacitor, or utilize resistor or capacitor materials formed as flexible films or layers coaxially on a wire or strut member.

Examples of the monitoring device 206 mounted on, or integrated in the structure of the endovascular prosthesis entails added mechanical functions shared with the rest of the endovascular prosthesis structure. For example, such an endovascular prosthesis includes the monitoring device such that it may:
1. be integrated into the mechanical structure of the endovascular prosthesis to create and maintain patency.
2. provide mechanical transduction of physiologic phenomena.
3. act as an antenna to receive RF energy then emit energy that is frequency shifted in response to a load.
4. be integrated with a monitoring system to track and communicate functions of endovascular prosthesis.

The monitoring device 206 integrated into the mechanical structure of the endovascular prosthesis may contribute to the mechanical structural reinforcement to create and maintain patency. The monitoring device 206 may also help anchor and secure the position of the endovascular prosthesis in the blood vessel. As such, the monitoring device 206 becomes load bearing with a load comparable to other segments in the endovascular prosthesis in terms of magnitude and vector. The load bearing of the monitoring device 206 contributes to creating and maintaining a luminal opening or patency; to implant fixation and maintenance of position with respect to anatomy. The monitoring device 206 may be integrated into existing structures and shapes of the endovascular prosthesis, and is space efficient so that structural elements are typically oriented in the optimal direction for stent/space ratio. Consequently, the load bearing is likely to be affected by changes to the loading on the wall of the artery or implant, which is ideal for the transduction function of the monitoring device 206.

In some implementations, the monitoring device 206 may function as a stand-alone implant that has no other purpose but to transduce, or to signal physical events.

In use with an endovascular prosthesis, the mounting or integration of the monitoring device 206 into the prosthesis may require consideration of the function of the prosthesis and the location of the placement. The monitoring device 206 may be used on any suitable type of endovascular prostheses, such as, a stent, a graft, or a stent-graft. Uses may also include on non-vascular structures, such as a stent or graft for a heart valve. In some application, the endovascular prosthesis 204 may bear more of a load than others, and in some, the endovascular prosthesis 204 may be subject to more twists and kinks. The method or technique used for mounting and/or integrating the monitoring device on the endovascular prosthesis 204 may affect the stability and performance of the monitoring device 206.

The monitoring device 206 may be mounted on the wall of the endovascular prosthesis 204 or integrated in the wall structure that may have one of many different forms. Stents, grafts, stent grafts, and other endovascular prostheses have wall structures that may take many forms. Different wall structures provide different advantages, such as the ability to allow cell re-growth in and around the wall structure, the ability to twist into the shape and path of the blood vessel or other tissue, and the ability to remain affixed in the location in which the device is mounted. The monitoring device 204 may be disposed in the selected wall structure without detracting from the features that make the selected wall structure suitable for the intended purpose.

FIGS. 3A and 3B illustrate an example of an endovascular prosthesis 300 with a monitoring device 302 disposed on the wall of the endovascular prosthesis 300. FIG. 3B is an exploded view of Detail A in FIG. 3A. The endovascular prosthesis 300 is a stent having rings connected at opposing points on the rings. One ring connects to a next ring at one point and to a previous ring at a point opposite the first point.

The monitoring device 302 is shown as a planar structure mounted or attached on the structure forming the wall of the endovascular prosthesis 300. In the example shown in FIGS. 3A and 3B, the connected ring structure of the stent may provide an antenna function so that the monitoring device may receive the first oscillating electrical signal and transmit the second oscillating electrical signal via the stent structure itself.

Figure 4A:
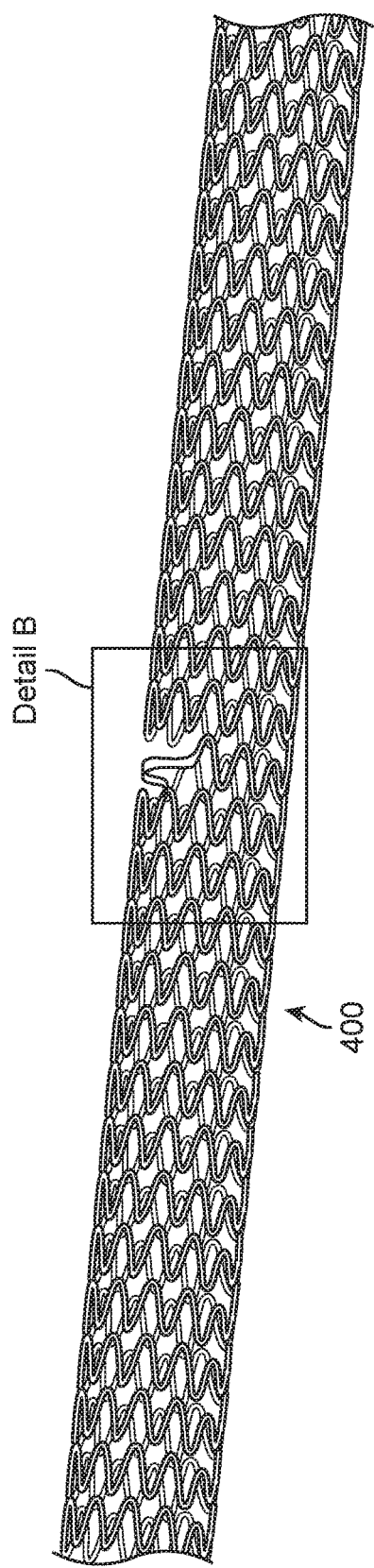
FIGS. 4A and 4B illustrate another example of an endovascular prosthesis with a monitoring device disposed on the wall of the endovascular prosthesis.
Figure 4B:
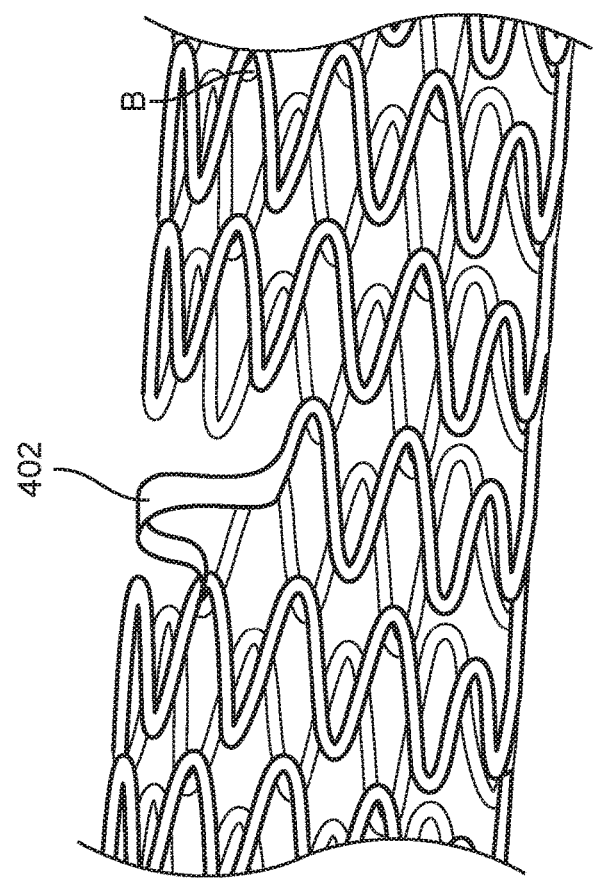

FIGS. 4A and 4B illustrate another example of an endovascular prosthesis 400 with a monitoring device 402 disposed on the wall of the endovascular prosthesis 400. FIG. 4B is an exploded view of Detail B in FIG. 4A. The endovascular prosthesis 400 in FIGS. 4A and 4B is formed with interconnecting struts where pairs of struts connect at corresponding apices to form a substantially ring-like structure. Each ring-like structure connects to one another by links at selected apices to extend the structure lengthwise with a lumen within the wall formed by the connected rings. The monitoring device 402 is shown as having a planar structure that is used as a link between the apex of one strut connection to another strut and the apex of another strut connection to another strut. As such, the monitoring device 402 is integrated into the wall structure and provides functions of contributing to patency and securing the position of the endovascular prosthesis 400.

Figure 5A:
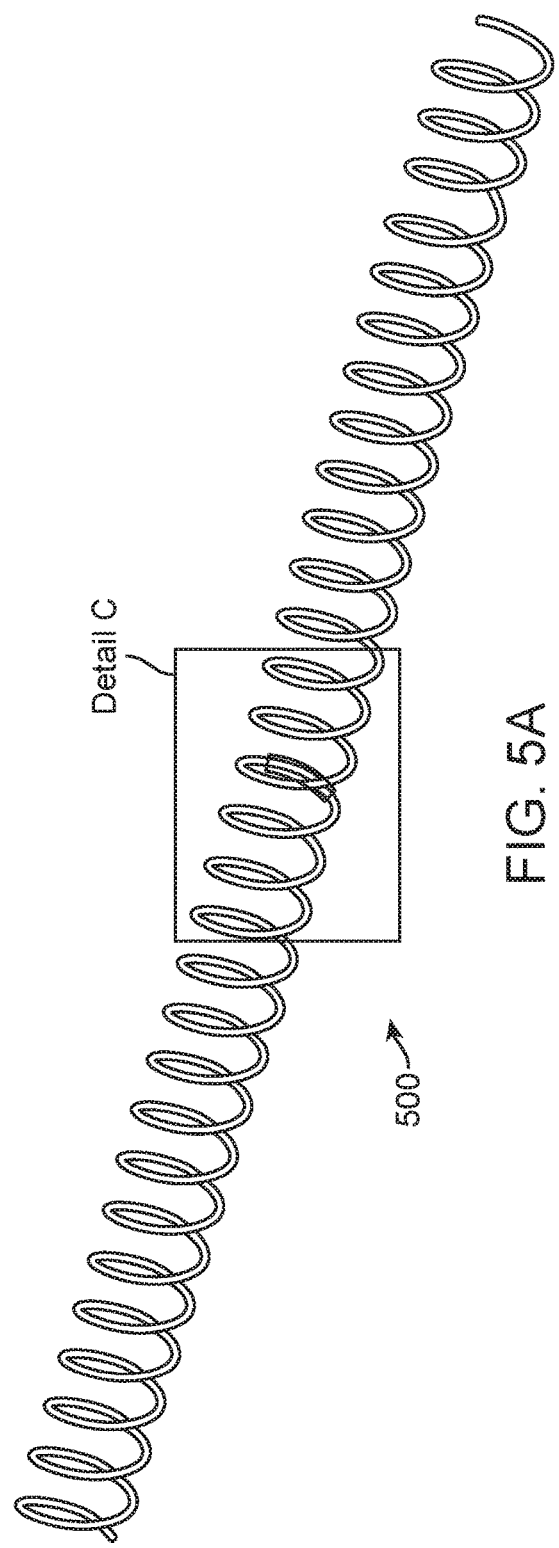
FIGS. 5A and 5B illustrate another example of an endovascular prosthesis with a monitoring device disposed on the wall of the endovascular prosthesis.
Figure 5B:
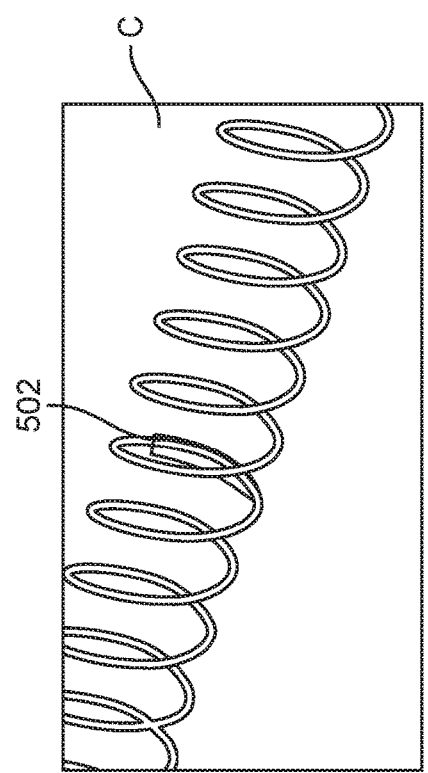

FIGS. 5A and 5B illustrate another example of an endovascular prosthesis 500 with a monitoring device 502 disposed on the wall of the endovascular prosthesis 500. FIG. 5B is an exploded view of Detail C in FIG. 5A. The endovascular prosthesis 500 is a stent having a coil structure. The monitoring device 502 may have a planar, flexible structure, or may be integrated in the wire-like structure that forms the coil.

Figure 6:
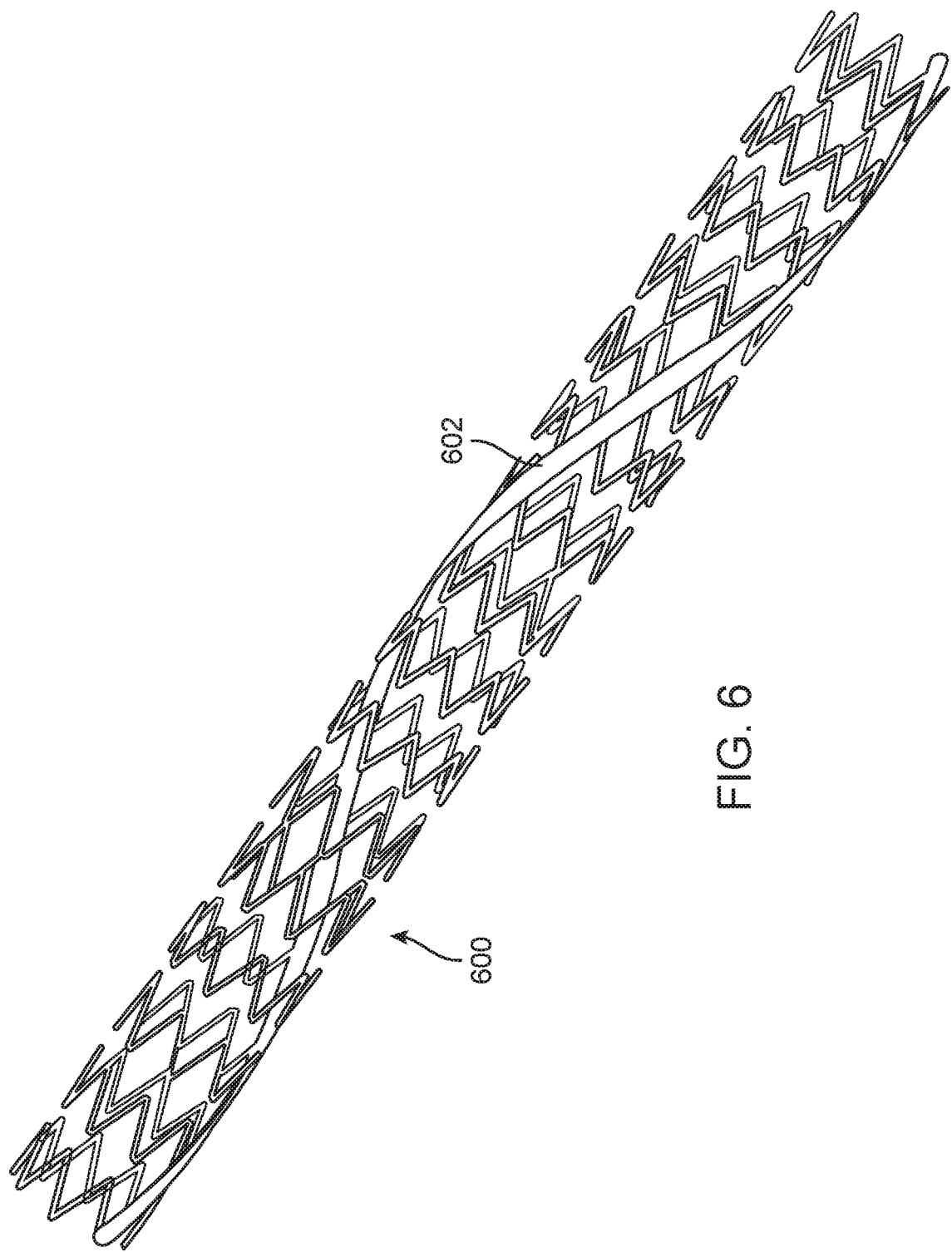
FIG. 6 illustrates another example of an endovascular prosthesis with a monitoring device disposed on the wall of the endovascular prosthesis.

FIG. 6 illustrates another example of an endovascular prosthesis 600 with a monitoring device 602 disposed on the wall of the endovascular prosthesis 600. The monitoring device 602 in FIG. 6 is formed as a tape or strip of film winding on the wall of the endovascular prosthesis 600. The tape structure may comprise a laminate, or film structure made of, for example, polyvinylidene difluoride ("PVDF"), metal layers, a fluorinated ethylene propylene ("HP") or polytetrafluoroethylene ("PTFE") jacket, which may be fused to a expanded PTFE ("ePTFE") surface of graft, or other suitable material, A PVDF layer may be poked. The poling may be performed on the film structure when mounted on the completed endovascular prosthesis 600.

Figure 7:
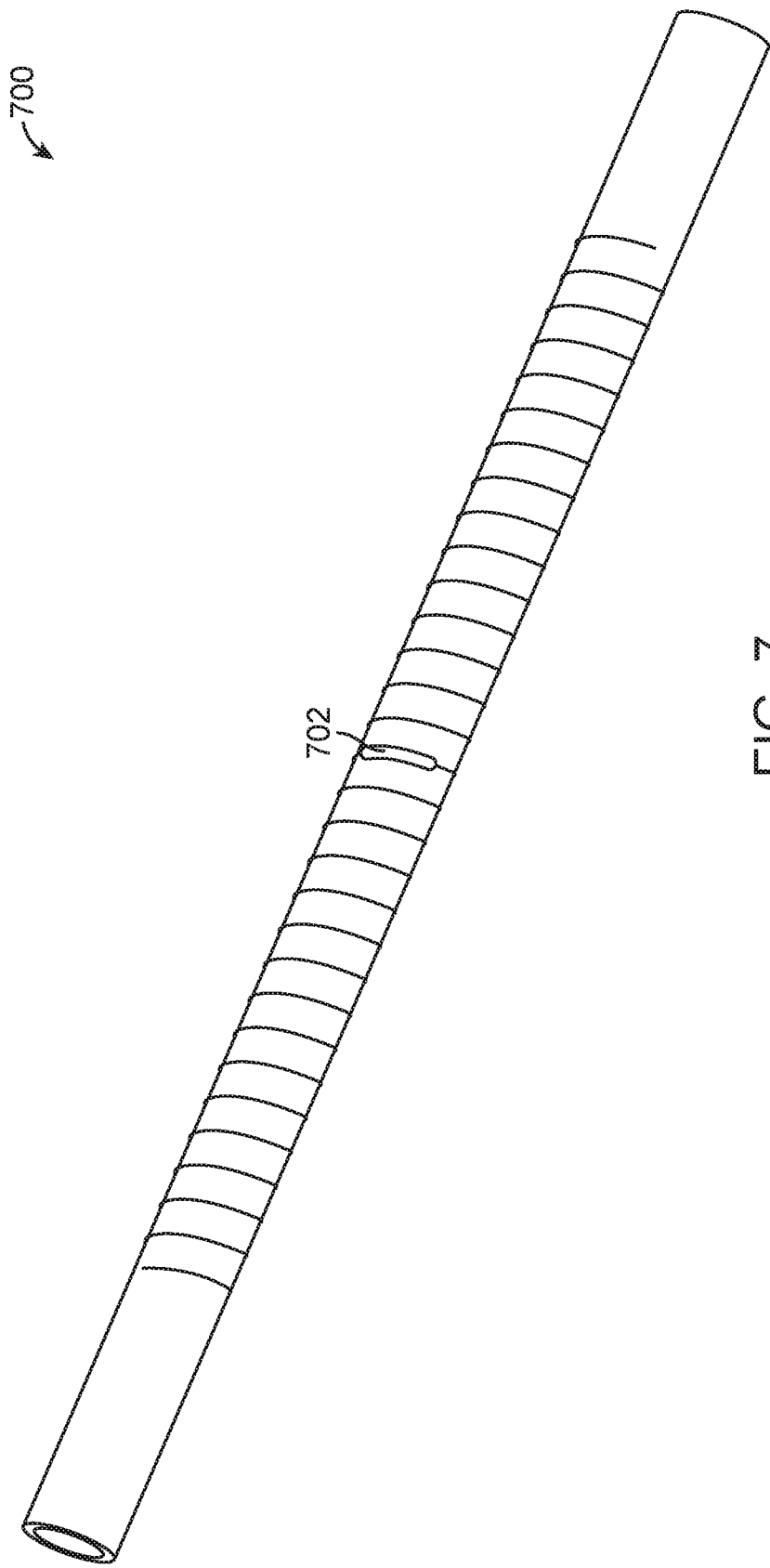
FIG. 7 illustrates another example of an endovascular prosthesis with a monitoring device disposed on the wall of the endovascular prosthesis.

FIG. 7 illustrates another example of an endovascular prosthesis 700 with a monitoring device 702 disposed on the wall of the endovascular prosthesis 700. The wall structure of the endovascular prosthesis 700 comprises a coiled flat structure with the monitoring device 702 mounted or integrated in the wall of the device. It is noted that the conduit shape of the endovascular prosthesis 700 where the structure forming the wall of the endovascular prosthesis includes a metallic component may provide the function of the antenna portion of the monitoring device. The antenna function may also be integrated into tube-like conduit structures with a metallic component, such as the endovascular prostheses illustrated in FIGS. 3A-6. It is noted that the endovascular prosthesis 700 may be made primarily of nitinol, which may not provide sufficient performance for an antenna structure. In endovascular prostheses made of nitinol, or another material lacking suitable desirable properties for an antenna, the endovascular prosthesis may be modified to include, for example, an antenna portion made of a material having desirable properties for an antenna. Gold would be desirable as an antenna portion due to its biocompatibility. An endovascular prosthesis may be made of any material capable of having a gold coating in a form suitable to provide an antenna function. In another example implementation, an antenna portion may be separately fabricated, then later integrated into the structure of the endovascular prosthesis. A gold antenna portion, for example, may be attached to the endovascular prosthesis by adhesive or other suitable attachment mechanism.

Figure 8:
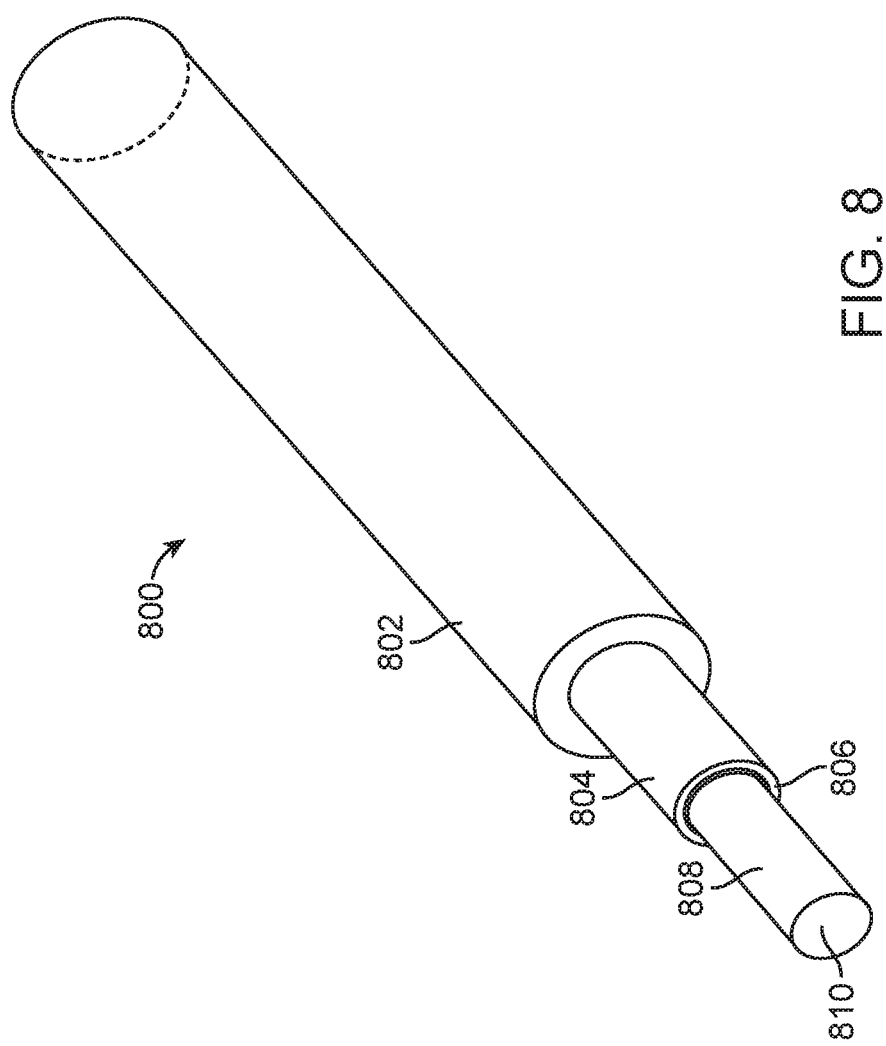
FIG. 8 illustrates an example of a sensor element for use in an example of an endovascular prosthesis where the sensor element is integrated in the structure of the endovascular prosthesis.

As noted above, the monitoring device may be mounted on or integrated in the structure of the endovascular prosthesis, where at least one or more of the components in the monitoring device are formed in the structure of the endovascular prosthesis. In one example, the antenna function may be performed by the metallic structure of the endovascular prosthesis as described above with reference to FIG. 7. The sensor element of the monitoring device may also be integrated with the structure of the endovascular prosthesis. FIG. 8 illustrates one example of an integrated sensor element 800 that is part of the structure of the endovascular prosthesis. The integrated sensor element 800 in FIG. 8 may form a wire-like structure, or a strut member having a circular or oval cross-section. The wire or strut may be configured into the structure of the endovascular prosthesis as described above, for example, in FIGS. 3A and 3B, 4A and 4B, and 5A and 5B.

The sensor element 800 includes an encapsulating tube 802, a first metallic coating 804, a poled PVDF tubing 806, a second metallic coating 808, and a metallic wire 810. The integrated sensor element 800 in FIG. 8 may operate as a piezoelectric sensor. The poled PVDF tubing 806 is a piezoelectric material disposed between the first metallic layer 804 and the second metallic layer 808 operating as conductors connected to the piezoelectric sensor. The PVDF tubing 806 is poled to bias the PVDF in a direction to develop charge and consequently, a voltage in proportion to the desired direction of the strain. The first metallic layer 804 and the second metallic layer 808 may be sputtered gold coatings. The encapsulating tube 802 may be a FEP or PTFE tubing fused to a ePTFE surface. The metallic wire 810 may be a nitinol metallic wire.

The integrated sensor element 800 may also operate as a variable capacitor or as a variable resistor where the the poled PVDF tubing 806 is replaced with another suitable insulator with variable capacitance properties or a resistor element. In the case of a variable capacitor, the first metallic layer 804, the suitable insulator 806, and the second metallic layer 808 form a coaxial capacitor. The coaxial capacitor may change capacitance in response to the pressure and/or stress on the endovascular prosthesis structure.

Figure 9:
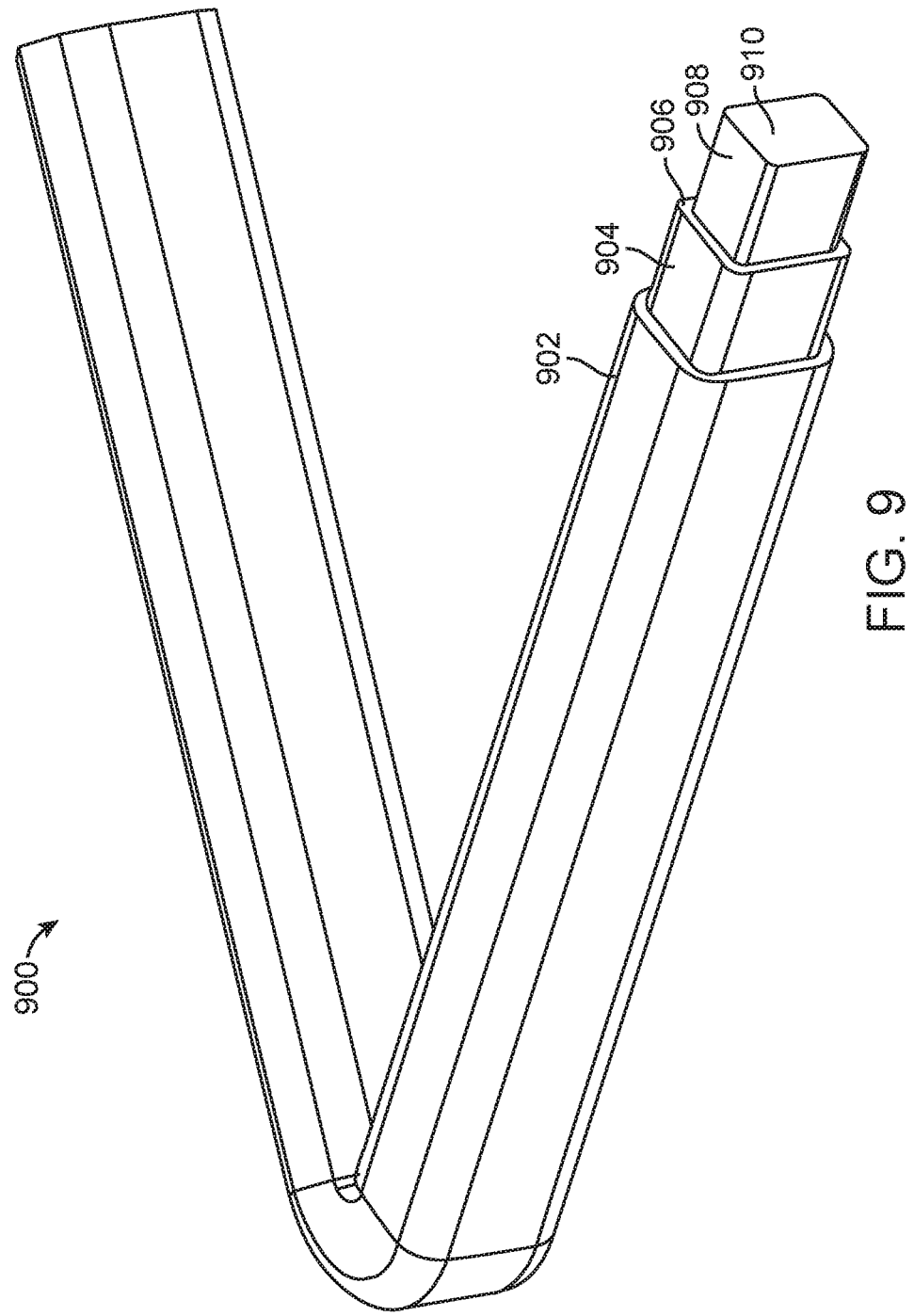
FIG. 9 illustrates another example of a sensor element for use in an example of an endovascular prosthesis where the sensor element is integrated in the structure of the endovascular prosthesis.

FIG. 9 illustrates another example of an integrated sensor element 900 for use in an example endovascular prosthesis. The integrated sensor element 900 in FIG. 9 may form a wire-like structure, or a strut member having a rectangular cross-section. In another example, the integrated sensor element 900 may be in the form of a laminate having layers fused on a surface of a strut or wire with rectangular cross-section. The wire or strut may be configured into the structure of the endovascular prosthesis as described above, for example, in FIGS. 3A and 3B, 4A and 4B, 5A and 5B, and 7.

The sensor element 900 includes an encapsulating layer 902, a first metallic coating 904, a poled PVDF layer 906, a second metallic coating 908, and a metallic strut 910. The integrated sensor element 900 in FIG. 9 may operate as a piezoelectric sensor. The poled PVDF tubing 806 is a piezoelectric material disposed between the first metallic layer 904 and the second metallic layer 908 operating as conductors connected to the piezoelectric sensor. The PVDF layer 906 is poled to bias the PVDF in a direction to develop charge and consequently, a voltage in proportion to the desired direction of the strain. The first metallic layer 904 and the second metallic layer 908 may be sputtered gold coatings. The encapsulating layer 902 may be a layer of a metal, parylene, FEP/PTFE/ePTFE/PVDF. The metallic strut 910 may be a nitinol metallic strut. The encapsulating layer 902 may also comprise a laminate structure having up to four layers of material, such as metal. Example laminates include titanium oxide, aluminum oxide, tantalum oxide, and silicon nitride in any combination. The encapsulating layer 902 may also be formed with a composite material.

The disclosure presented herein may be considered in view of the following example embodiments:

Example 1. An endovascular prosthesis comprising: a conduit forming a lumen within a surrounding wall having an inner surface and an outer surface; and a monitoring device disposed on the wall forming the lumen, the monitoring device comprising a sensor element configured to detect a physical event and to generate an electrical parameter shift in response to the physical event, and an antenna portion configured to receive a first oscillating electrical signal from an interrogator device and to transmit a second oscillating electrical signal to the interrogator device where the second oscillating electrical signal is modulated by the electrical parameter shift.

Example 2. The endovascular prosthesis of Example 1 further comprising: a sensor controlled oscillator configured to generate the second oscillating electrical signal where the electrical parameter shift of the sensor element determines a modulated frequency of the second oscillating electrical signal.

Example 3. The endovascular prosthesis of Example 1 where the electrical parameter shift is in response to pressure or strain on the sensor element.

Example 4. The endovascular prosthesis of claim 1 where the sensor controlled oscillator is a passive resonant circuit, where the electrical parameter shift by the sensor element in response to the physical event is a change in capacitance that varies the modulated frequency of the second oscillating electrical signal.

Example 5. The endovascular prosthesis of claim 1 where the sensor controlled oscillator is a resistor controlled oscillator, where the electrical parameter shift by the sensor element in response to the physical event is a change in resistance that varies the modulated frequency of the second oscillating electrical signal.

Example 6. The endovascular prosthesis of claim 5 where the resistor controlled oscillator is a Wein Bridge Oscillator.

Example 7. The endovascular prosthesis of claim 1 where the sensor controlled oscillator is a voltage controlled oscillator, where electrical parameter shift by the sensor element in response to the physical event is a change in resistance that varies the modulated frequency at the output of the voltage controlled oscillator.

Example 8. The endovascular prosthesis of claim 1 where the sensor element is any one of either a piezoresistive sensor, a piezoelectric strain gauge, or a variable capacitive sensor.

Example 9. The endovascular prosthesis of claim 4 where the passive resonant circuit is a ring oscillator.

Example 10. The endovascular prosthesis of claim 1 further comprising: a passive power source configured to collect and store electrical energy from the first oscillating electrical signal.

Example 11. The endovascular prosthesis of claim 1 further comprising a radio frequency identification detection mechanism configured to transmit an identifier of the device when energized by the first electrical oscillating signal.

Example 12. The endovascular prosthesis of claim 1 where: the wall of the endovascular prosthesis is formed by at least one of the following: a plurality of coaxially disposed rings connected by at least one link; a helix structure; a braided structure; a coil structure; a structure of interconnected struts; and the monitoring device is disposed on the wall of the endovascular prosthesis.

Example 13. The endovascular prosthesis of claim 1 where the monitoring device is disposed within the wall of the endovascular device.

Example 14. The endovascular prosthesis of claim 1 where the endovascular prosthesis comprises at least one component of the monitoring device integrated within a structure of the endovascular prosthesis.

Example 15. The endovascular prosthesis of claim 14 where the sensor element is an integrated sensor element formed as a coaxial capacitor comprising a first metallic conduit, a second metallic conduit, and a sensor material that changes in capacitance when subject to pressure or stress, the coaxial capacitor forming at least a portion of a wire or strut element configured to form the wall structure of the endovascular prosthesis.

Example 16. The endovascular prosthesis of claim 14 where the sensor element is an integrated sensor element formed as a variable resistor comprising a sensor material that varies in resistance when subject to pressure or stress disposed between a first metallic conduit and a second metallic conduit, the variable resistor forming at least a portion of a wire or strut element configured to form the wall structure of the endovascular prosthesis.

Example 17. The endovascular prosthesis of claim 15 where the sensor material includes polyvinylidene difluoride ("PVDF").

Example 18. The endovascular prosthesis of claim 14 where at least a portion of the endovascular prosthesis is made of a metal, and at least a portion of the endovascular prosthesis made of metal is configured to operate as the antenna portion of the monitoring device.

Example 19. The endovascular prosthesis of claim 14 where at least a part of the monitoring device is a circuit disposed on a film disposed on the wall of the endovascular prosthesis.

Example 20. The endovascular prosthesis of claim 14 where at least a part of the monitoring device is a circuit integral with the wall of the endovascular prosthesis.

Example 21. An endovascular prosthesis comprising: a conduit formed by a wall structure surrounding a lumen; a sensor element configured to generate an electrical parameter shift in response to a physical event, the sensor element integrated in the wall structure of the conduit.

Example 22. The endovascular prosthesis of claim 21 where: the wall structure comprises at least one wire structure, where at least a part of the wire structure comprises: a first metallic conduit; a second metallic conduit; and a sensor material formed in a tubular shape disposed between the first metallic conduit and the second metallic conduit, where the first and second metallic conduits are conductors in a monitoring device detecting the electrical parameter shift in the sensor material.

Example 23. The endovascular prosthesis of claim 22 where the sensor is a variable capacitive sensor, and the first metallic conduit and the second metallic conduit form the electrodes of the variable capacitor.

Example 24. The endovascular prosthesis of claim 22 where the sensor material is a variable resistance material configured to generate a resistance change in response to the physical event.

Example 25. The endovascular prosthesis of claim 22 where the sensor material is a poled PVDF material configured to generate a voltage change in response to the physical event.

Example 26. The endovascular prosthesis of claim 21 where: the wall structure comprises at least one strut structure, where at least a part of the strut structure comprises: a first metallic layer; a second metallic layer; and a sensor material formed in layer disposed between the first metallic layer and the second metallic layer, where the first and second metallic layers are conductors in a monitoring device detecting the electrical parameter shift in the sensor material.

Example 27. The endovascular prosthesis of claim 26 where the sensor material is an insulator for forming a variable capacitive sensor, and the first metallic layer and the second metallic layer form the electrodes of the variable capacitor.

Example 28. The endovascular prosthesis of claim 22 where the sensor material is a variable resistance material configured to generate a resistance change in response to the physical event.

Example 29. The endovascular prosthesis of claim 22 where the sensor material is a poled PVDF material configured to generate a voltage change in response to the physical event.

Example 30. The endovascular prosthesis of claim 22 where the sensor element is enclosed in an encapsulating layer.

Example 31. The endovascular prosthesis of claim 30 where the encapsulating layer is a laminate.

Example 32. The endovascular prosthesis of claim 30 where the encapsulating layer is made of a composite material.

Example 33. The endovascular prosthesis of claim 30 where the encapsulating layer is formed as layer material selected from polyvinylidene difluoride ("PVDF"), a metal, fluorinated ethylene propylene ("FEP"), polytetrafluoroethylene ("PTFE"), parylene, and expanded PTFE.

Example 34. The endovascular prosthesis of claim 30 where the encapsulating layer is formed as a laminate structure comprising up to four materials including any combination of titanium oxide, aluminum oxide, tantalum oxide, and silicon nitride.

Example 35. The endovascular prosthesis of claim 30 where the encapsulating layer is formed as a composite material consisting of any combination of titanium oxide, aluminum oxide, tantalum oxide, and silicon nitride.

Example 36. The endovascular prosthesis of claim 21 where the sensor element is formed on a wire or strut structure made of a metal.

Example 37. The endovascular prosthesis of claim 36 where the metal of the wire or strut structure is nitinol.

Example 38. A sensor element configured to operate in a monitoring device while integrated in a structure of an endovascular prosthesis, the sensor element comprising: a first metallic part; a second metallic part; and a sensor material formed between the first metallic part and the second metallic part, where the first and second metallic parts are conductors in a monitoring device detecting the electrical parameter shift in the sensor material, and where the first and second metallic parts and the sensor material are integrated with a wall structure of the endovascular prosthesis.

Example 39. A method comprising: receiving a first electrical oscillating signal at a portion of an endovascular prosthesis structure operating as an antenna, the endovascular prosthesis comprising a sensor element; sensing a physical event using the sensor element; modulating a second electrical oscillating signal using an electrical parameter shift generated by the sensor element in response to the physical event; and transmitting the modulated second electrical oscillating signal using the portion of the endovascular prosthesis structure operating as an antenna.

It is noted that the PVDF sensor material may be replaced by an alternative transducing material, such as a piezoresistive material, or other suitable alternatives. The PVDF sensor material may also be replaced by a suitable insulator to form a variable capacitor sensor, or with a resistive material to operate as a variable resistor.

The figures and block diagrams in the different depicted examples illustrate the architecture, functionality, and operation of some possible implementations of apparatuses and methods in an illustrative example. In this regard, each block in the flowcharts or block diagrams may represent a module, a segment, a function, a portion of an operation or step, some combination thereof.

In some alternative implementations of an illustrative example, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

The description of the different illustrative examples has been presented for purposes of illustration and description, and is not intended to be exhaustive or limited to the examples in the form disclosed. Many modifications and variations will be apparent to those of ordinary skill in the art. Further, different illustrative examples may provide different features as compared to other desirable examples. The example or examples selected are chosen and described in order to best explain the principles of the examples, the practical application, and to enable others of ordinary skill in the art to understand the disclosure for various examples with various modifications as are suited to the particular use contemplated.

What is claimed is:

1. An endovascular prosthesis for implantation in a blood vessel comprising:
    a conduit forming a lumen within a surrounding wall having an inner surface and an outer surface; and
    a monitoring device disposed on the wall forming the lumen, the monitoring device comprising a sensor element configured to detect blood flow parameters in the blood vessel and generating an electrical parameter shift in response to the blood flow parameters, and an antenna portion configured to receive a first oscillating electrical signal from an interrogator device and to transmit a second oscillating electrical signal to the interrogator device where the second oscillating electrical signal is modulated by the electrical parameter shift;
    at least one component of the monitoring device being integrated within a structure of the endovascular prosthesis, and wherein the sensor element is an integrated sensor element comprising a first metallic conduit, a second metallic conduit, and a sensor material, the sensor element forming at least a portion of a wire or strut element configured to form the wall structure of the endovascular prosthesis; and wherein the sensor element is formed as a coaxial capacitor, where the sensor material changes in capacitance when subject to pressure or stress, or the sensor element is formed as a variable resistor, where the sensor material is disposed between the first metallic conduit and the second metallic conduit and varies in resistance when subject to pressure or stress.

2. The endovascular prosthesis of claim 1 further comprising:
a sensor controlled oscillator configured to generate the second oscillating electrical signal where the electrical parameter shift of the sensor element determines a modulated frequency of the second oscillating electrical signal.

3. The endovascular prosthesis of claim 1 where the electrical parameter shift is in response to pressure or strain on the sensor element.

4. The endovascular prosthesis of claim 1 where the sensor controlled oscillator is a passive resonant circuit, where the electrical parameter shift by the sensor element in response to the blood flow parameters is a change in capacitance that varies the modulated frequency of the second oscillating electrical signal.

5. The endovascular prosthesis of claim 1 where the sensor controlled oscillator is a resistor controlled oscillator, where the electrical parameter shift by the sensor element in response to the blood flow parameters is a change in resistance that varies the modulated frequency of the second oscillating electrical signal.

6. The endovascular prosthesis of claim 1 where the sensor controlled oscillator is a voltage controlled oscillator, where electrical parameter shift by the sensor element in response to the blood flow parameters is a change in resistance that varies the modulated frequency at the output of the voltage controlled oscillator.

7. The endovascular prosthesis of claim 1 where the sensor element is any one of either a piezoresistive sensor, a piezoelectric strain gauge, or a variable capacitive sensor.

8. The endovascular prosthesis of claim 4 where the passive resonant circuit is a ring oscillator.

9. The endovascular prosthesis of claim 1 further comprising:
a passive power source configured to collect and store electrical energy from the first oscillating electrical signal.

10. The endovascular prosthesis of claim 1 further comprising a radio frequency identification detection mechanism configured to transmit an identifier of the device when energized by the first electrical oscillating signal.

11. The endovascular prosthesis of claim 1 where:
the wall of the endovascular prosthesis is formed by at least one of the following:
a plurality of coaxially disposed rings connected by at least one link;
a helix structure;
a braided structure;
a coil structure;
a structure of interconnected struts; and
the monitoring device is disposed on the wall of the endovascular prosthesis.

12. The endovascular prosthesis of claim 1 where at least a portion of the endovascular prosthesis is made of a metal, and at least a portion of the endovascular prosthesis made of metal is configured to operate as the antenna portion of the monitoring device.

* * * * *